United States Patent
Shah et al.

(10) Patent No.: US 8,105,299 B2
(45) Date of Patent: *Jan. 31, 2012

(54) EXTRUSION BLOW-MOLDED CORPOREAL PORT MOUNTING STRUCTURE

(75) Inventors: Tilak M. Shah, Cary, NC (US); Dylan Hege, Cary, NC (US); Jessica K. Crews, Raleigh, NC (US)

(73) Assignee: Polyzen Inc., Apex, NC (US)

( * ) Notice: Subject to any disclaimer, the term of this patent is extended or adjusted under 35 U.S.C. 154(b) by 523 days.

This patent is subject to a terminal disclaimer.

(21) Appl. No.: 12/106,760

(22) Filed: Apr. 21, 2008

(65) Prior Publication Data

US 2008/0262450 A1 Oct. 23, 2008

Related U.S. Application Data

(60) Provisional application No. 60/913,538, filed on Apr. 23, 2007.

(51) Int. Cl.
*A61F 5/44* (2006.01)
(52) U.S. Cl. ........ 604/339; 604/327; 604/328; 604/332; 604/338; 604/341; 604/342; 604/343
(58) Field of Classification Search .................. 604/339, 604/338, 341, 342, 343, 327, 328, 332
See application file for complete search history.

(56) References Cited

U.S. PATENT DOCUMENTS

| | | | | | |
|---|---|---|---|---|---|
| 3,447,533 | A | * | 6/1969 | Spicer | 600/32 |
| 3,659,611 | A | | 5/1972 | Miller | |
| 3,848,602 | A | * | 11/1974 | Gutnick | 606/193 |
| 3,915,171 | A | * | 10/1975 | Shermeta | 604/101.05 |
| 4,022,216 | A | * | 5/1977 | Stevens | 604/101.03 |
| 4,043,345 | A | | 8/1977 | Kramann et al. | |
| 4,311,146 | A | | 1/1982 | Wonder | |
| 4,327,736 | A | * | 5/1982 | Inoue | 604/101.05 |
| 4,464,175 | A | | 8/1984 | Altman et al. | |

(Continued)

FOREIGN PATENT DOCUMENTS

JP 51-090376 A 8/1976

(Continued)

OTHER PUBLICATIONS

Co-pending U.S. Appl. No. 12/106,743 entitled,"Ostomy Bag Mounting Structure," filed Apr. 21, 2008 in the name of Tilak M. Shah.

*Primary Examiner* — Tatyana Zalukaeva
*Assistant Examiner* — Ginger T Chapman
(74) *Attorney, Agent, or Firm* — Kelly K. Reynolds; Hultquist, PLLC; Steven J. Hultquist

(57) ABSTRACT

A mounting structure for installation at a corporeal port opening. The mounting structure includes mounting structure for installation at a corporeal port opening, such mounting structure including a blowmolded article comprising enlarged cylindrical sections interconnected by tube segments, adapted to engage the corporeal port opening at a tube segment intermediate the enlarged cylindrical sections and with the enlarged cylindrical sections being in abutting contact with internal and external corporeal surfaces surrounding said port opening. The mounting structure is useful employed for anchoring of a therapeutic device such as an ostomy bag at a corresponding port of the body, with the enlarged sections of the device providing effective anchoring of the mounting structure and permitting the mounting structure to be comfortably worn by a patient during therapeutic intervention.

21 Claims, 5 Drawing Sheets

U.S. PATENT DOCUMENTS

| | | | |
|---|---|---|---|
| 4,555,242 A * | 11/1985 | Saudagar | 604/103.08 |
| 4,650,463 A | 3/1987 | LeVeen et al. | |
| 4,662,890 A * | 5/1987 | Burton | 623/1.31 |
| 4,664,114 A * | 5/1987 | Ghodsian | 606/193 |
| 4,685,901 A * | 8/1987 | Parks | 604/103.03 |
| 4,693,236 A * | 9/1987 | Leprevost | 600/32 |
| 4,705,502 A * | 11/1987 | Patel | 604/544 |
| 4,721,508 A * | 1/1988 | Burton | 604/338 |
| 4,784,133 A | 11/1988 | Mackin | |
| 4,836,204 A * | 6/1989 | Landymore et al. | 606/215 |
| 4,941,869 A * | 7/1990 | D'Amico | 600/32 |
| 4,976,692 A * | 12/1990 | Atad | 604/101.03 |
| 5,116,310 A | 5/1992 | Seder et al. | |
| 5,219,792 A | 6/1993 | Kim et al. | |
| 5,234,454 A | 8/1993 | Bangs | |
| 5,360,414 A | 11/1994 | Yarger | |
| 5,433,252 A | 7/1995 | Wolf et al. | |
| 5,527,280 A | 6/1996 | Goelz | |
| 5,545,220 A | 8/1996 | Andrews et al. | |
| 5,656,013 A * | 8/1997 | Yoon | 600/207 |
| 5,679,423 A | 10/1997 | Shah | |
| 5,782,800 A * | 7/1998 | Yoon | 604/514 |
| 5,807,333 A | 9/1998 | Osborne et al. | |
| 5,833,915 A | 11/1998 | Shah | |
| 5,879,499 A | 3/1999 | Corvi | |
| 5,924,456 A | 7/1999 | Simon | |
| 5,935,115 A * | 8/1999 | Espina | 604/277 |
| 5,951,514 A | 9/1999 | Sahota | |
| 5,996,639 A | 12/1999 | Gans et al. | |
| 6,022,313 A | 2/2000 | Ginn et al. | |
| 6,249,708 B1 | 6/2001 | Nelson et al. | |
| 6,270,477 B1 | 8/2001 | Bagaoisan et al. | |
| 6,291,543 B1 | 9/2001 | Shah | |
| 6,352,077 B1 | 3/2002 | Shah | |
| 6,409,741 B1 | 6/2002 | Crocker | |
| 6,460,541 B1 | 10/2002 | Shah et al. | |
| 6,478,789 B1 | 11/2002 | Spehalski et al. | |
| 6,663,646 B1 | 12/2003 | Shah | |
| 6,712,832 B2 | 3/2004 | Shah | |
| 6,805,662 B2 | 10/2004 | Shah et al. | |
| 6,827,710 B1 | 12/2004 | Mooney et al. | |
| 6,875,193 B1 | 4/2005 | Bonnette et al. | |
| 6,960,199 B2 | 11/2005 | Burkett et al. | |
| 7,112,186 B2 | 9/2006 | Shah | |
| 7,182,745 B2 * | 2/2007 | Desmond, III | 604/8 |
| 7,220,252 B2 | 5/2007 | Shah | |
| 7,470,251 B2 | 12/2008 | Shah | |
| 7,721,742 B2 * | 5/2010 | Kalloo et al. | 600/115 |
| 2003/0088209 A1 | 5/2003 | Chiu et al. | |
| 2005/0222329 A1 | 10/2005 | Shah | |
| 2006/0058576 A1 * | 3/2006 | Davies et al. | 600/32 |
| 2006/0129094 A1 | 6/2006 | Shah | |
| 2006/0212064 A1 | 9/2006 | Shah | |
| 2007/0212559 A1 | 9/2007 | Shah | |
| 2007/0239110 A1 | 10/2007 | Shah | |
| 2007/0299463 A1 | 12/2007 | Shah | |
| 2008/0188802 A1 | 8/2008 | Shah | |
| 2008/0262449 A1 * | 10/2008 | Shah et al. | 604/339 |
| 2008/0262450 A1 | 10/2008 | Shah | |
| 2009/0082724 A1 | 3/2009 | Shah et al. | |

FOREIGN PATENT DOCUMENTS

| | | |
|---|---|---|
| JP | 51-100833 A | 9/1976 |
| JP | 51-101084 A | 9/1976 |
| JP | 10-127771 A | 5/1998 |

* cited by examiner

EXTRUSION BLOW-MOLDED CORPOREAL PORT MOUNTING STRUCTURE

CROSS-REFERENCE TO RELATED APPLICATIONS

This application claims the benefit of priority under the provisions of 35 U.S.C. §120 of U.S. Provisional Patent No. 60/913,538 filed Apr. 23, 2007 in the names of Tilak M. Shah, et al.

FIELD OF THE INVENTION

The present invention relates to a mounting structure that may be employed to fixture a port to the body of a subject for therapeutic or physiological intervention. In one embodiment, the invention relates to an ostomy bag mounting structure.

DESCRIPTION OF THE RELATED ART

In the treatment of a variety of disease states and physiological conditions, and in the course of medical intervention, it may be necessary to establish a portal at the surface of the human body to which can be joined a monitoring or treatment device, flow circuitry, etc.

One such circumstance involves the affixation to the body of an ostomy bag for removal of wastes of an individual. The ostomy bag requires a portal to which the bag can be secured to the individual. The portal includes an anchoring structure to which the ostomy bag can be coupled in waste-receiving relationship to the body of the wearer of the bag.

Prior portal structures have been unsatisfactory from the perspective of comfort of the individual accessorized with such structure, due to the sensitivity of the stoma. In addition, the portal structures of the prior art are frequently difficult to install on the body of the subject, so that they are properly anchored for subsequent use.

The present invention addresses such deficiencies.

SUMMARY OF THE INVENTION

The present invention relates to a mounting structure that may be employed to fixture a port to the body of a subject for therapeutic or physiological intervention.

The invention provides a mounting structure that is readily mountable on the body of a subject, in a safe, efficient and ready manner, and that in subsequent use is very comfortable to the wearer.

The invention in one aspect relates to a mounting structure for installation at a corporeal port opening, such mounting structure including an extrusion blowmolded article comprising enlarged cylindrical sections interconnected by tube segments, adapted to engage the corporeal port opening at a tube segment intermediate said enlarged cylindrical sections and with the enlarged cylindrical sections being in abutting contact with internal and external corporeal surfaces surrounding said port opening.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention relates to a mounting structure that may be employed to fixture a port to the body of a subject for therapeutic or physiological intervention. In one embodiment, the invention relates to an ostomy bag mounting structure.

Figure 1:
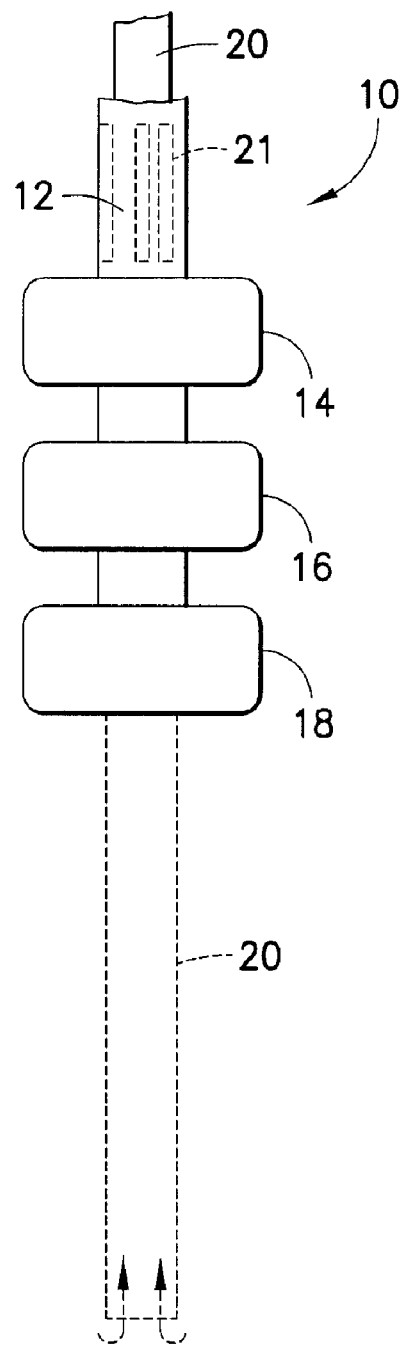
FIG. 1 is a schematic elevation view of an extrusion blow-molded mounting structure, according to one embodiment of the present invention.

FIG. 1 is a schematic elevation view of an extrusion blow-molded mounting structure 10, according to one embodiment of the present invention. Although extrusion blow molding is primarily described herein in respect of the blow molded articles of the invention, it is to be appreciated that such articles can in all instances be formed by tube blow molding.

As illustrated, the mounting structure of FIG. 1 includes a central tube 12 including tube segments integrally formed with enlarged sections 14, 16 and 18 of the structure. Each of the enlarged sections 14, 16 and 18 is of cylindrical form and hollow in character, communicating with the central opening of the tube segments of the tube 12.

The structure shown in FIG. 1 is extrusion blow molded, using a correspondingly shaped extrusion blow molding die that after the extrusion blow molding operation is opened to extract the extrusion blow molded article shown in FIG. 1.

The extruded tube 20 is as shown inserted reentrantly into the tube 12 and extracted from the other end of the tube 12, so that it protrudes from such tube. One of the tubes 12 and 20 may be formed with longitudinally extending ribs or lumens 21, so that when the tubes 12 and 20 are coaxially arranged with one another, the ribs or lumens serve to stiffen the structure and make it resistant to collapsing when installed on the body of a patient.

The extrusion blow molded article of FIG. 1, and other mounting structures of the invention, can be formed using any suitable extrusion blow molding apparatus. Alternatively, the article of the invention can be formed by tube blow molding in which a uniform diameter is placed in a mold and pressurized internally with a blowing fluid to expand the original tube into conformity with the mold shape.

The molded article can be formed of any suitable thermoplastic polymeric material, including, for example, polyethylene, polytetrafluoroethylene, polypropylene, polyurethane, polyvinylchloride, polyamide, polyether amide elastomer, styrenic elastomer, styrene isoprene butadiene (SIB)/styrene ethylene butadiene (SEB), and copolymers of monomers of the foregoing, etc., with polyurethane in general being preferred. The polymeric material used in forming the mounting structure of the invention may for example comprise a thermoplastic elastomer (TPE) material, and/or multilayer film, e.g., a laminate including barrier film, tie layers, and exterior layers.

Figure 2:
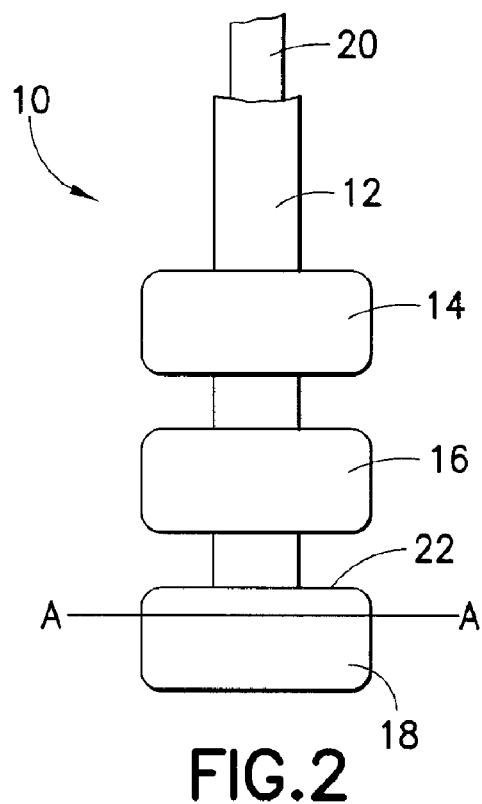
FIG. 2 is an elevation view of the extrusion blow-molded mounting structure shown in FIG. 1, illustrating the severing of the lower enlarged section, to form a corresponding flange element of the structure.

FIG. 2 is an elevation view of the extrusion blow-molded mounting structure 10 shown in FIG. 1, illustrating the severing of the lower enlarged section 18 along the line indicated by arrows A-A, to form a corresponding flange element 22 of the structure.

Figure 3:
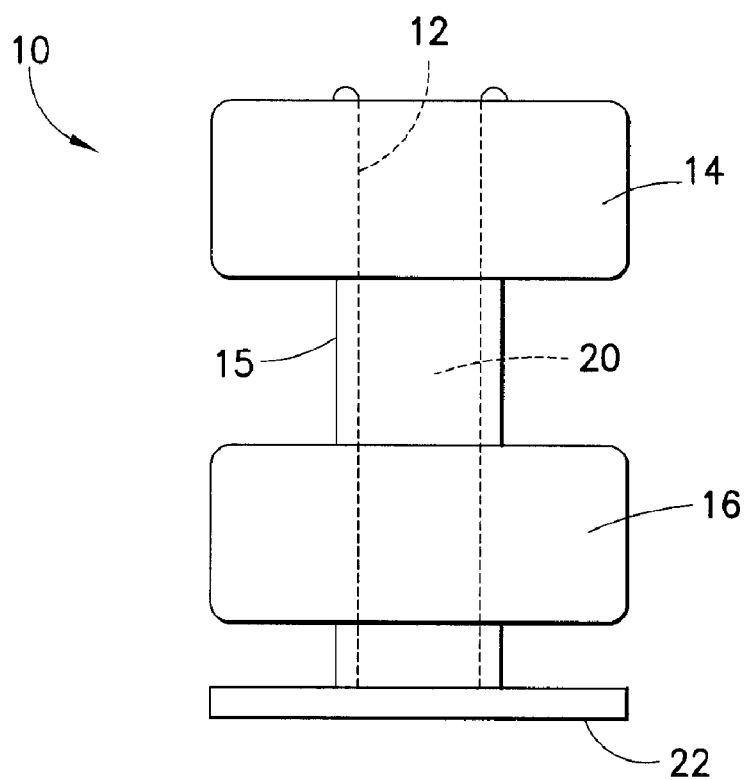
FIG. 3 is an elevation view of the mounting structure of FIG. 2, subsequent to the severing of the lower enlarged section to form a corresponding flange element.

FIG. 3 is an elevation view of the mounting structure of FIG. 2, subsequent to the severing of the lower enlarged section to form a corresponding flange element, except with the tube 12 everted over tube 20. All parts and elements are numbered correspondingly in FIG. 3 to the same parts and features as specified in FIGS. 1 and 2. The mounting structure thereby provides a coaxial tube section 15 between the enlarged sections 14 and 16. The flange element 22 permits the mounting structure to be readily coupled to other structures for mating and engagement therewith.

Figure 4:
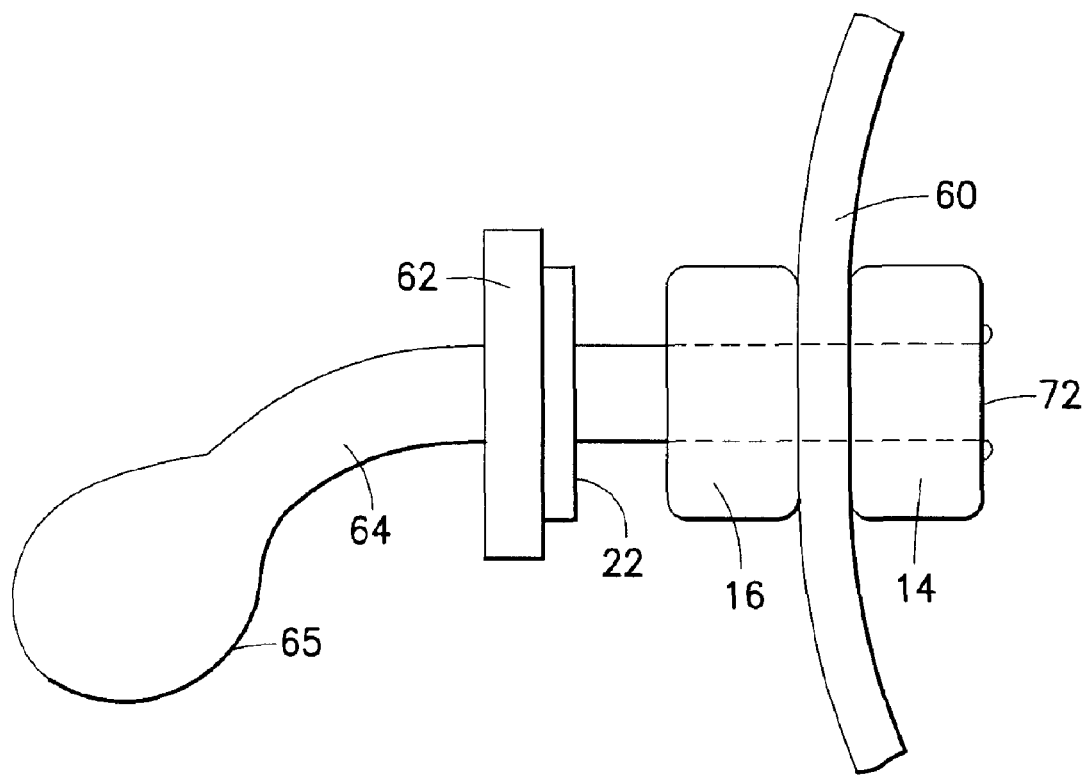
FIG. 4 is a perspective view of an extrusion blow-molded mounting structure of the invention, as mounted in a corporeal port and attached at the flange element thereof to a catheter.

FIG. 4 is a perspective view of an extrusion blow-molded mounting structure of the invention, as mounted in a corporeal port and attached at the flange element thereof to a catheter.

As illustrated, the extrusion blow-molded mounting structure is positioned with the upper enlarged section positioned inside the abdominal wall 60, with the coaxial tube oriented to present the open end of the central opening 72 to the interior body cavity. The intermediate enlarged section 16 is disposed externally of the abdominal wall, and the tube segment therebetween is reposed in a port opening (not shown) in the abdominal wall. The flange 22 formed by severing the lower enlarged section 18 of the originally blow molded article is mated with a coupling 62 at the proximal end of a catheter 64 that in turn is secured to an ostomy bag 65.

The extrusion blow molded or tube blow molded mounting structure of the invention is advantageously formed of a thin film (less than 25 mils thickness) polymeric material, of sufficient thickness and composition to be flexible and resilient in character, but to retain the general shape of the enlarged sections and tube segments associated therewith, in the use of the mounting structure.

The extrusion blow molded mounting structure is comfortable to wear, and accommodates the sensitivity of the stoma.

It will be appreciated that the extrusion blow molded mounting structure may be formed with four successive enlarged sections, of which the first and last are severed to form respective flange elements, in the manner described in connection with FIGS. 2 and 3. By such provision, the mounting structure has a flange element interiorly disposed in the body, such as may be advantageous to provide a bearing surface or "stop" for the assembly so that it is maintained in proper position in the body cavity, as well as a flange element that is exterior to the body, for coupling or engagement with flow circuitry and/or other structure.

The severing of an enlarged section to form a flange element may be carried out with a rotary cutting tool that serves to sever the side surface of the enlarged section as the mounting structure subsequent to molding thereof is rotated to accommodate such severing. Alternatively, the extrusion blow molding mold may be fabricated with a circumscribing cutting surface in the mold cavity that serves to sever the enlarged section as it is being extrusion-formed in the mold.

The latter approach may require an additional tool or tool modification to remove the severed remainder of the enlarged section from the mold.

The polymeric film used in the mounting structure of the invention may in specific embodiments comprise a thermoplastic elastomeric material, such as a polyurethane film material, or a laminate including barrier film, tie layers, and exterior layers.

The extrusion blow molded mounting structure may be of any suitable dimensions, and may for example have a thickness in a range of from about one mil up to 50 mils, with diameter of the enlarged sections being from 0.75 inch to 2.5 inches or more, in specific embodiments of the invention.

The invention therefore provides a mounting structure characterized by enlarged sections of an extrusion blow molded article that may be reposed against the surfaces on either side or at both sides of the port through which the intermediate tube segment of the mounting structure is inserted. The mounting structure can be readily installed, to provide a mounting structure at the port that is comfortable and avoids the deficiencies of prior port structures.

Figure 5:
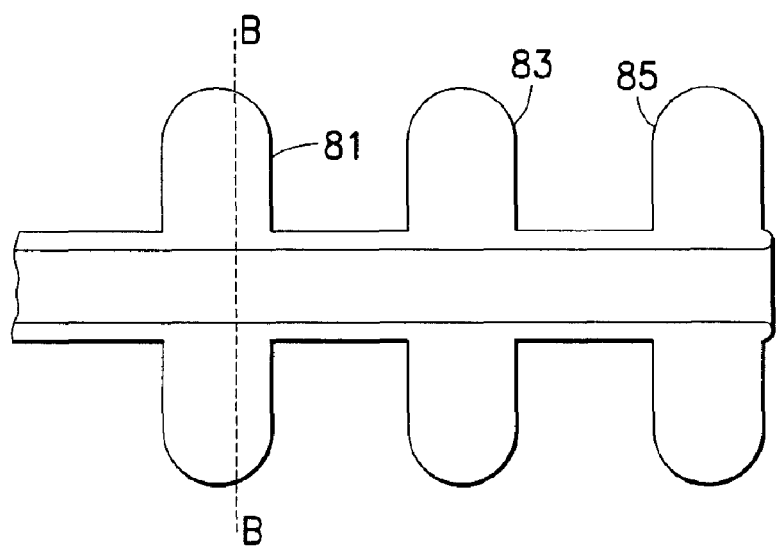
FIG. 5 is a schematic cross-section side elevation view of a mounting structure according to another embodiment of the invention.

FIG. 5 is a schematic cross-section side elevation view of a mounting structure according to another embodiment of the invention, comprising an article including three blow-molded enlarged sections 81, 83 and 85. As shown, the tubing has been reentrantly inserted to form a coaxial tube structure. In this embodiment, the balloon 81 is shown with a dashed severing line B-B, which is severed to form a flange element, for coupling of the mounting structure with a connector or other coupled element or structure.

Figure 6:
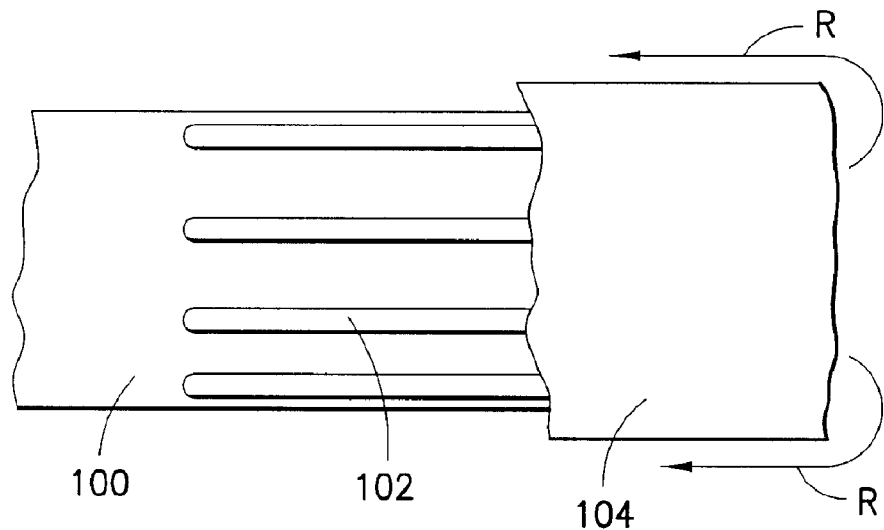
FIG. 6 is a schematic perspective view of an eversion operation in which a ribbed surface of a tube is being overlaid by an everted tube segment to dispose the rib elements between the resulting coaxial tube segments.

FIG. 6 is a schematic perspective view of an eversion operation in which a ribbed surface of a tube 100 is being overlaid by an everted tube segment 104 to dispose the rib elements 102 between the resulting coaxial tube segments.

Figure 7:
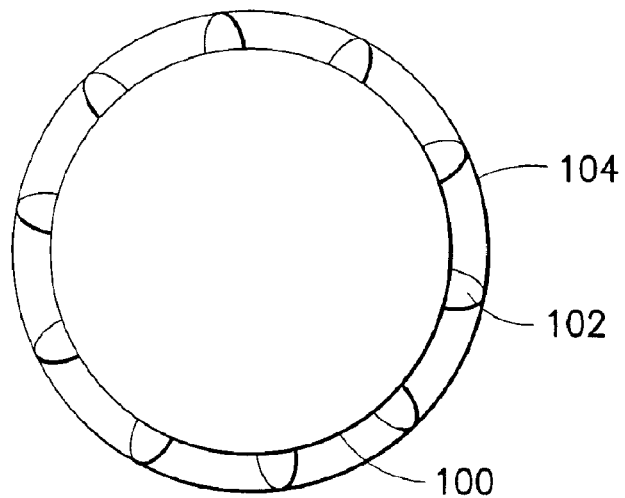
FIG. 7 is a cross-sectional view of the coaxial tube segments resulting from the eversion operation illustrated in FIG. 6.

FIG. 7 is a cross-sectional view of the coaxial tube segments 101 and 104 resulting from the eversion operation illustrated in FIG. 6, with the rib elements 102 disposed therebetween.

In lieu of the rib elements shown in FIGS. 6 and 7, lumen passages may be formed by longitudinally heat sealing a polymeric film, so that a lumen is formed. Alternatively, the coaxial tubing structure may be formed and subjected to longitudinal welding at space-apart intervals, to provide stiffening and reinforcement lumen passages. Such passages may be inflated with a suitable fluid, e.g., air or water, to impart improved sturdiness to the coaxial structure and enhanced comfort of the mounting structure when installed in a corporeal port. The lumen passages can be inflated or otherwise be of such dimensional character as to provide the requisite stiffening and reinforcement of the coaxial tube structure. Any number of rib or lumen elements may be employed for such purpose, e.g., 2-4, 6, 8, 12, or 16.

Figure 8:
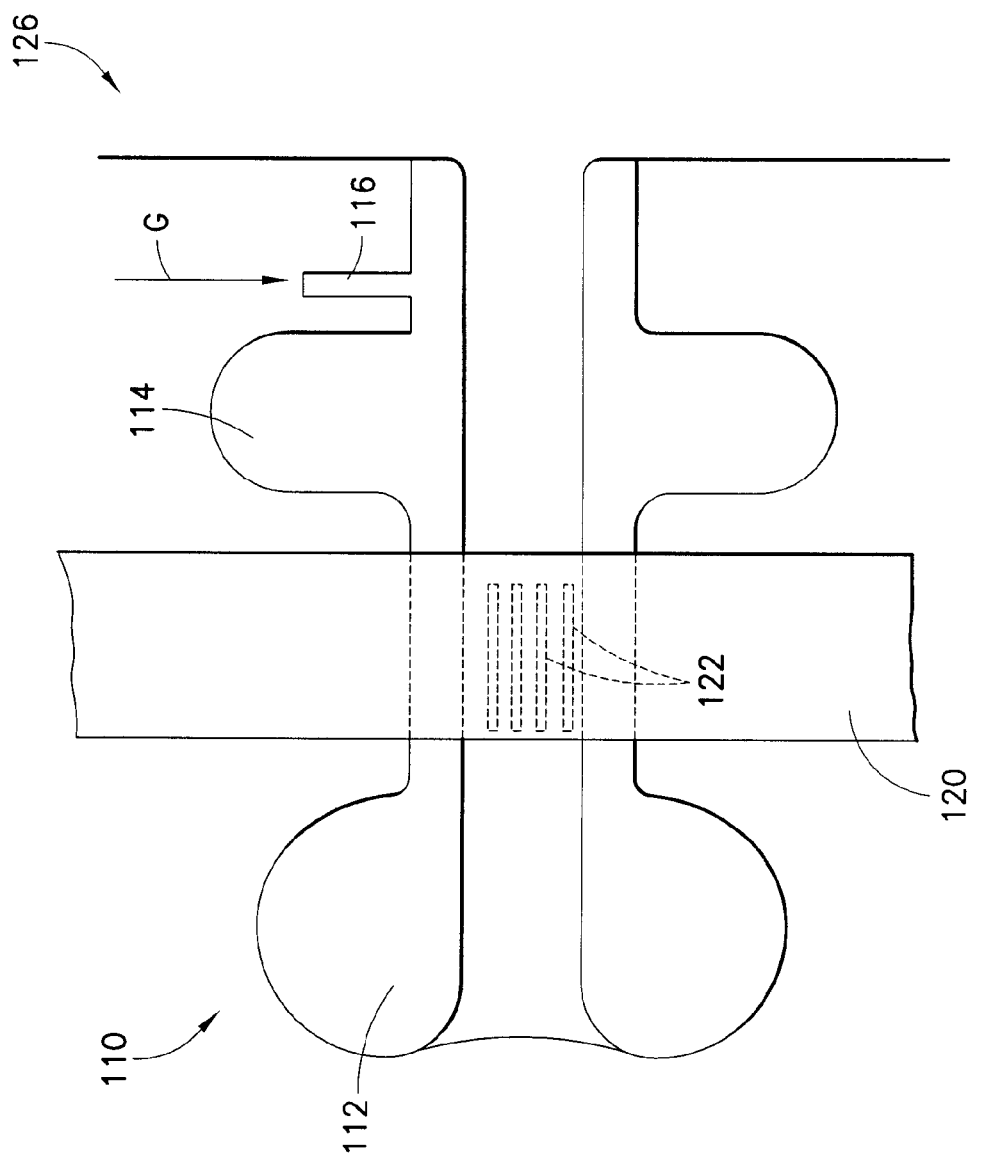
FIG. 8 is a schematic representation of a mounting structure according to one embodiment of the invention, as installed on the body of a wearer.

FIG. 8 is a schematic representation of a mounting structure 110 according to one embodiment of the invention, as installed on the body of a wearer. The mounting structure comprises an interior enlarged section 112 and exterior enlarged section 114, with longitudinal, spaced apart ribs 122 in the coaxial tubing annular space to provide increased stiffness and resistance to collapse. The intermediate coaxial tubing section is inserted through a port opening in the abdominal wall 120.

The mounting structure includes an inflation port 116, to which a source of inflation fluid, such as compressed air or water, maybe coupled to inflate the enlarged sections, both interior and exterior, subsequent to initial installation of the mounting structure in the corporeal port. The mounting structure shown in FIG. 8 has been initially formed with a third enlarged section that has been severed to form the flange 126. The flange permits coupling with an external catheter, colostomy bag, or other apparatus, as appropriate to the therapeutic intervention associated with such mounting structure.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A mounting structure for installation at a corporeal port opening, said mounting structure including a blowmolded article comprising enlarged cylindrical sections interconnected by flexible everted tube segments, wherein said mounting structure comprises a central longitudinal opening such that the article is open at both ends, the article adapted to mount to the corporeal port opening at a tube segment intermediate to said enlarged cylindrical sections and with the enlarged cylindrical sections arranged for abutting contact with internal and external corporeal surfaces surrounding said port opening.

2. The mounting structure of claim 1, formed of a thermoplastic polymeric thin-film material.

3. The mounting structure of claim 2, wherein said thermoplastic polymeric thin-film material comprises a polymer selected from the group consisting of polyethylene, polytetrafluoroethylene, polypropylene, polyurethane, polyvinylchloride, polyamide, polyether amide elastomer, styrenic elastomer, styrene isoprene butadiene (SIB)/styrene ethylene butadiene (SEB), and copolymers of monomers of the foregoing.

4. The mounting structure of claim 2, wherein said thermoplastic polymeric thin-film material comprises a thermoplastic elastomer (TPE) material.

5. The mounting structure of claim 2, wherein said thermoplastic polymeric thin-film material comprises a laminate.

6. The mounting structure of claim 5, wherein said laminate comprises a barrier film, tie layer, and exterior layer.

7. The mounting structure of claim 1, as coupled with an ostomy bag.

8. The mounting structure of claim 2, wherein said thermoplastic polymeric thin-film material has a thickness of less than 25 mils.

9. The mounting structure of claim 1, including between an adjacent pair of enlarged sections a coaxial tubing portion comprising longitudinal ribs or longitudinal luminal passages external to the central longitudinal opening and internal to the everted tube segments.

10. The mounting structure of claim 1, including an integral flange.

11. The mounting structure of claim 9, wherein said longitudinal ribs or longitudinal luminal passages are adapted to be inflated in use.

12. The mounting structure of claim 11, wherein said longitudinal ribs or longitudinal luminal passages are inflated with an inflation medium.

13. The mounting structure of claim 12, wherein said inflation medium comprises air or water.

14. The mounting structure of claim 1, comprising a single enlarged section, and a coaxial tubing portion, and a flange.

15. The mounting structure of claim 1, comprising two enlarged sections, with a coaxial tubing portion therebetween.

16. The mounting structure of claim 15, wherein said coaxial tubing portion is reinforced by longitudinal ribs or longitudinal lumens.

17. The mounting structure of claim 15, further comprising a flange.

18. The mounting structure of claim 1, formed by extrusion blow molding.

19. The mounting structure of claim 1, formed by tube blow molding.

20. The mounting structure of claim 1, wherein the flexible everted tube segments comprise coaxial tubes.

21. The mounting structure of claim 20, wherein the coaxial tubes have longitudinally extending ribs or lumens therebetween.

\* \* \* \* \*